United States Patent [19]

Hellring et al.

[11] Patent Number: 6,002,059
[45] Date of Patent: Dec. 14, 1999

[54] PROCESS FOR UPGRADING NATURAL GAS

[75] Inventors: Stuart D. Hellring, Pittsburgh, Pa.; Scott A. Stevenson, Houston, Tex.

[73] Assignee: Mobil Oil Corporation, Fairfax, Va.

[21] Appl. No.: 09/181,834

[22] Filed: Oct. 28, 1998

[51] Int. Cl.$^6$ .................................................. C07C 2/00
[52] U.S. Cl. ........................ 585/500; 585/310; 585/943; 423/352; 423/400; 423/402; 423/403; 423/404; 423/405
[58] Field of Search .................................. 585/500, 310, 585/943; 423/400, 402, 403, 404, 405, 352, 359

[56] References Cited

U.S. PATENT DOCUMENTS

| | | | |
|---|---|---|---|
| 1,946,114 | 2/1934 | Schlecht et al. | 423/404 |
| 3,110,563 | 11/1963 | Krauss et al. | 423/403 |
| 3,872,025 | 3/1975 | Singleton | 423/359 |
| 3,947,551 | 3/1976 | Parrish | 423/359 |
| 4,124,687 | 11/1978 | Whelan | 423/404 |
| 4,199,533 | 4/1980 | Benson | 585/500 |
| 4,213,954 | 7/1980 | Pinto | 423/359 |
| 4,238,468 | 12/1980 | Bonacci et al. | 423/359 |
| 4,298,588 | 11/1981 | Pinto | 423/359 |
| 4,376,105 | 3/1983 | Matuda et al. | 423/400 |
| 4,433,192 | 2/1984 | Olah | 585/709 |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,465,893 | 8/1984 | Olah | 585/709 |
| 4,467,130 | 8/1984 | Olah | 585/709 |
| 4,495,374 | 1/1985 | Jones et al. | 585/500 |
| 4,499,322 | 2/1985 | Jones et al. | 585/500 |
| 4,499,323 | 2/1985 | Gaffney | 585/500 |
| 4,499,324 | 2/1985 | Gaffney | 585/500 |
| 4,547,610 | 10/1985 | Sofranko et al. | 585/500 |
| 4,634,800 | 1/1987 | Withers et al. | 585/500 |
| 4,670,619 | 6/1987 | Withers et al. | 585/500 |
| 4,695,668 | 9/1987 | Velenyi | 585/500 |
| 4,720,377 | 1/1988 | Pennington | 423/400 |
| 4,879,427 | 11/1989 | Sofranko | 585/500 |
| 4,879,727 | 11/1989 | Ramesh et al. | 375/76 |
| 5,068,486 | 11/1991 | Han et al. | 585/500 |
| 5,093,542 | 3/1992 | Gaffney | 585/500 |
| 5,146,027 | 9/1992 | Gaffney | 585/500 |
| 5,406,017 | 4/1995 | Withers et al. | 585/500 |

*Primary Examiner*—Walter D. Griffin
*Attorney, Agent, or Firm*—Penny L. Prater; Malcolm D. Keen

[57] ABSTRACT

The invention discloses a method for converting methane to higher order hydrocarbons. This method includes synthesizing ammonia from natural gas and nitrogen in the presence of a source of hydrogen. The ammonia is converted to nitrous oxide in the presence of a source of oxygen. Methane is coupled in the presence of the nitrous oxide to provide higher hydrocarbons. The invention also discloses a method of balancing reaction heat requirements in a process for converting methane to higher order hydrocarbons.

7 Claims, No Drawings

PROCESS FOR UPGRADING NATURAL GAS

BACKGROUND OF THE INVENTION

This invention relates to utilizing natural gas as a fundamental component for the production of higher order hydrocarbons, and, in particular, to a unique conversion scheme using nitrous oxide as an agent for joining methane groups contained in natural gas to produce such hydrocarbons.

Natural gas is an abundant fossil fuel resource. Recent estimates place worldwide natural gas reserves at about $35 \times 10^{14}$ standard cubic feet, corresponding to the energy equivalent of about 637 billion barrels of oil.

A major source of methane is natural gas. Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

A significant portion of the known natural gas reserves is associated with fields found in remote, difficultly accessible regions. Many of these distant sources are not amenable to transport by pipeline. For example, sources that are located in areas requiring economically unfeasible pipeline networks or in areas requiring transport across large bodies of water are not amenable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such processing, and with proper procedures, safely stored or transported. These processes, which involve liquefying natural gas at a temperature of about −162° C., transporting the gas, and revaporizing it, are complex and energy intensive.

Still another approach has been the conversion of natural gas to higher order hydrocarbons that can be easily handled and transported. The term "higher order hydrocarbon" refers to a hydrocarbon having at least two carbon atoms. In this way easily transportable commodities may be derived directly from natural gas at the wellhead. The conversion of natural gas to higher order hydrocarbons, especially ethane and ethylene, retains the material's versatility for use as precursor materials in chemical processing. Known processes are available for the further conversion of ethane and ethylene to other useful materials.

U.S. Pat. No. 4,199,533 discloses a process for converting methane to higher molecular weight hydrocarbons by using chlorine gas as a recyclable catalyst. The process produces ethylene as a major product along with hydrogen chloride, which is converted to chlorine for recycle in the system. Major drawbacks of the '533 process are the large amount of chlorine required, the necessity of regenerating chlorine from hydrogen chloride to maintain an economically viable system, and the need to use operating temperatures in excess of 1000° C. to produce ethylene. Additionally, the required chlorine is corrosive under such operating conditions.

Methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regeneration of a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See U.S. Pat. Nos. 4,443,649; 4,444,984; 4,443,648; 4,443,645; 4,443,647; 4,443,644; and 4,443,646. Also see U.S. Pat. Nos. 4,499,323 and 4,499,324.

U.S. Pat. No. 4,499,322 and U.S. Pat. No. 4,495,374 disclose and claim a process for the conversion of methane to higher hydrocarbon which comprises contacting methane with an oxidative synthesizing agent containing a promoting amount of alkali metal and/or compounds thereof.

Hinsen and Baerns report studies of a continuous mode for the oxidative coupling of methane wherein regenerating air is cofed with the methane feed. Hinsen, W. and Baerns, M., "Oxidative Koppling von Methan zu $C_2$-Kohlenwasserstoffen in Gegenwart unterschiedlicher Katalysatoren", Chemiker-Zeitung, Vol. 107, No. 718, pp. 223–226 (1983). Using a catalyst based on lead oxide and gamma-alumina in a fixed bed reactor operated at 1 atmosphere total pressure and 600.degree.–750° C., they report results of approximately 53% selectivity to ethane and ethylene at 8% methane conversion for a feed consisting of about 50% methane, 25% air and 25% nitrogen. Other metal oxides studies by Hinsen and Baerns included oxides of Bi, Sb, Sn and Mn.

Commonly-assigned U.S. patent application Ser. No. 600,656, filed Apr. 16, 1984, discloses and claims a process for converting methane to higher hydrocarbons by contacting methane and an oxygen-containing gas with a solid which includes a reducible metal oxide and an alkali/alkaline earth metal promoter.

Commonly-assigned U.S. patent application Ser. No. 600,670, filed Apr. 16, 1984, discloses and claims a process for converting methane to higher hydrocarbons by contacting methane and an oxygen-containing gas with a manganese silicate.

Oxidative condensation of methane in the presence of solid superacid catalysts is disclosed in U.S. Pat. Nos. 4,433,192; 4,465,893; and 4,467,130. European Published Patent Application 93,543 discloses a process for aromatizing methane wherein a methane feedstock and an oxidizing agent other than molecular oxygen are contacted at temperatures of about 10° to 600° C. with a solid acidic catalyst having Bronsted acid sites.

Oxidative conversion of methane to higher hydrocarbons by contacting a mixture of methane and a gaseous oxidant with a catalyst contact solid which does not contain a reducible metal oxide in the presence of a chalcogen promoter is disclosed in U.S. Pat. No. 4,879,427.

Despite these advances in the art of oxidative conversion of methane to higher hydrocarbons, a disadvantage has been the general decline in activity and selectivity achieved with various contact agents over time. The reaction products of such processes include a significant amount of carbon oxides, coke and water. Thus, these processes are not adequately selective for higher hydrocarbons. It would be beneficial to increase methane conversions and increase selectivities to the desired hydrocarbon products.

Selectivity for higher order hydrocarbons can be improved by contacting a gas comprising methane with oxides of nitrogen. U.S. Pat. No. 5,406,017 discloses such a reaction in the presence of a nonacidic solid catalyst at a temperature within the range of about 700° to 1200° C. However, the use of oxides of nitrogen may make the process economically unfeasible.

There are at least two conventional commercial methods for the production of nitrous oxide. By one method, nitrous oxide is produced catalytically from ammonia and air using pelletized Mn and Bi oxides as catalysts, reportedly with an 85 percent conversion of ammonia per single pass at 310–350° C. This method is disclosed in a Japanese technical publication entitled "SYNTHESIS OF NITROUS OXIDE BY OXIDATION OF AMMONIA", by T. Suwa, A. Matsushima, Y. Suziki and Y. Namina in Kohyo Kagaku Zasshi, Vol. 64, pp. 1879–1888, 1961 and also in Czech. Patent CS 186,313, issued Nov. 30, 1973 to J. Mikoda, see Chemical Abstract 95(22); 189,494a. The feed gas composition used in this patent was calculated to contain about 2 percent ammonia in 98 percent air and the exit gas concentration of nitrous oxide was about 1 percent. On this basis, the nitrous oxide produced must be separated from a much larger volume of air, resulting in relatively high separation costs. In addition, this catalytic method for producing nitrous oxide from ammonia produces several by-product nitrogen compounds such as nitric oxide and nitrogen dioxide which necessitate additional separation steps.

The second conventional commercial method for the production of nitrous oxide involves the thermal decomposition of ammonium nitrate at about 170° C. according to the equation below:

$$NH_4NO_3 \rightarrow N_2O + 2H_2O$$

This method is described in Kirk-Othmer's Encyclopedia of Chemical Technology, Volume 2, p.527, (1978). Since ammonium nitrate is considered to be a high explosive, precautions must be taken to minimize the risk of explosion when using this production method, including feeding a concentrated aqueous solution of ammonium nitrate into a reactor at 275° C. However, any dry, molten ammonium nitrate in the system that becomes heated above 250° C. poses a detonation risk according to the equation:

$$NH_4NO_3 \rightarrow N_2 + \tfrac{1}{2}O_2 + 2H_2O$$

Besides the above two commercial methods for making nitrous oxide, various laboratory methods have also been disclosed. For example, molten nitrate salts have been reported to react with ammonium chloride to produce nitrous oxide, chloride ion, and water according to the equation below:

$$NH_4Cl + NO_3^- \rightarrow Cl^- + 2H_2O + N_2O$$

Such a reaction is reported in a technical publication by H. Fouzanfar and D. H. Kerridge in J. Inorg. Nucl. Chem., Volume 40, pp. 1327–1330. This reaction leaves a chloride ion residue in the melt and, with extensive reaction over time, the chloride can build up and actually convert the nitrate melt into a chloride melt. Moreover, the presence of chloride ion can lead to well-known corrosion problems with stainless steels and other conventional materials of reactor construction.

U.S. Pat. No. 4,720,377 discloses a method for producing nitrous oxide by a reaction of ammonia with at least one molten nitrate salt of an alkaline earth metal at reaction conditions to produce nitrous oxide. However, this process is not conducted with high activity.

On the basis of the above, an inexpensive safe method for producing nitrous oxide with high activity would be highly desirable.

The present invention overcomes difficulties presently encountered in the art by providing a method by which to convert natural gas to higher order hydrocarbons with high activity and selectivity.

SUMMARY

The present invention provides a method for converting methane to higher order hydrocarbons. This method includes synthesizing ammonia from natural gas and nitrogen in the presence of a source of hydrogen. The ammonia is converted to nitrous oxide in the presence of a source of oxygen. Methane is coupled in the presence of the nitrous oxide to provide higher hydrocarbons. The source of hydrogen is steam reformed methane.

The present invention also provides a method of balancing reaction heat requirements in a process for converting methane to higher order hydrocarbons. This method includes transferring the heat of reaction resulting from the conversion of ammonia to nitrous oxide and the heat of reaction resulting from the coupling methane in the presence of nitrous oxide to an endothermic synthesis reaction of ammonia from natural gas and nitrogen. This synthesis reaction is upstream from the conversion reaction and provides the ammonia to the conversion.

The present invention further provides a method of producing nitrous oxide. This method includes reacting ammonia and nitric oxide in the presence of a molybdenum-containing catalyst. In a preferred embodiment the molybdenum-containing catalyst is supported on zirconia. The molybdenum-containing catalyst can include molybdenum in an amount of from about 3% molybdenum by weight to about 20% molybdenum by weight, preferably from about 7% molybdenum by weight to about 15% molybdenum by weight, and most preferably 10% molybdenum by weight to 13% molybdenum by weight. The selectivities to nitrous oxide are more than 70% by this method. The nitric oxide for this reaction can be obtained by the oxidation of ammonia over a Pt catalyst.

An advantage of the present invention is that it provides a method by which natural gas can be converted to higher order hydrocarbons with high activity and selectivity, and at a lower cost than current methods. Such a method allows the upgrading of natural gas in areas where it is plentiful but transportation costs can make production uneconomical.

The high selectivity and activity of this method is partially achieved by using nitrous oxide as the oxidative agent for the coupling of methane. The lower cost of conversion is partially achieved by the novel combination of reactions. The lower cost is also achieved by integrating the reaction heat requirements of the individual steps of the process for converting methane to higher order hydrocarbons. Additionally, the present invention provides nitrous oxide for the oxidative conversion of methane to higher order hydrocarbons at a lower cost than current methods. Moreover, nitrous oxide is produced with higher activity and selectively via the method of the present invention than via current methods.

Current methods of oxidative conversion of methane to higher order hydrocarbons, which involve contacting methane with oxygen or oxides of metals, result in products which are not adequately selective for higher order hydrocarbons. The reaction products of such processes include a significant amount of carbon oxides, coke and water. The use of nitrogen oxides for oxidative conversion significantly improves the selectivity for higher order hydrocarbons. However, current methods which use oxides of nitrogen may make the conversion process economically unfeasible. Moreover, current methods of producing nitrous oxide have low selectivity and activity.

DETAILED DESCRIPTION

The present invention provides a method for converting methane to higher hydrocarbons. This process relies on the novel combination of reactions.

The preferred stoichiometry for this process is:

$$3CH_4 + 6H_2O \rightarrow 12H_2 + 3CO_2 \quad (1a)$$

$$12H_2 + 4N_2 \rightarrow 8NH_3 \quad (1b)$$

$$4NH_3 + 5O_2 \rightarrow 4NO + 6H_2O \quad (2)$$

$$4NH_3 + 4NO + 3O_2 \rightarrow 4N_2O + 6H_2O \quad (3)$$

$$4CH_4 + 4N_2O \rightarrow 2C_2H_4 + 4N_2 + 4H_2O \quad 7CH_4 + 8O_2 \rightarrow 2C_2H_4 + 3CO_2 + 10H_2O \quad (4)$$

In this scheme, ammonia, nitric oxide and nitrous oxide are intermediates that are consumed in intervening reactions prior to the final product. The net reaction primarily involves the conversion of methane and oxygen to ethylene, carbon dioxide and water.

The cost of natural gas feedstock is more than 90% of the variable costs and approximately two-thirds of the cash cost of production of ammonia for a typical U.S. Gulf Coast facility. Costs are significantly reduced in locations where natural gas is produced as a by product or can be readily obtained. The present invention provides a novel combination of reactions by which natural gas can be upgraded to higher order hydrocarbons. The availability of inexpensive natural gas allows for the production of low-cost nitrous oxide via the reaction of ammonia and nitric oxide. This nitrous oxide is then used to couple methane into ethylene or other higher hydrocarbon products.

The method of the present invention includes synthesizing ammonia from natural gas and nitrogen in the presence of a source of hydrogen. (Steps 1a and 1b.) The primary commercial method for ammonia synthesis which uses the steam reforming of methane as a source of hydrogen (e.g., Bakemeier, et al., "Ammonia", in Ullmann's Encyclopedis of Industrial Chemistry, vol. 2.638–91, 1992) can be used in the present invention.

The next step of this method is the oxidation of ammonia to nitric oxide (Step 2). Preferably, the conversion is done over a Pt catalyst at a pressure of three to six atmospheres and a temperature of about 900° C. (e.g., Thiemann, M., Shiebler, E., and Wiegand, K. W., "Nitric Acid, Nitrous Acid and Nitrogen Oxides," from Ullmann's Encyclopedia of Industrial Chemistry, vol. A17, 293–339, 1992). Selectivities to nitric oxide of 95% to 98% are typically obtained.

The next step of the present invention is the production of nitrous oxide.

Nitrous oxide maybe produced by the reaction of ammonia and nitric acid (Step 3). This reaction can be carried out with high activity and selectivity over molybdenum-containing catalysts. In a preferred embodiment, the molybdenum is supported on zirconia. The molybdenum-containing catalyst can include molybdenum in an amount of from about 3% molybdenum by weight to about 20% molybdenum by weight, preferably from about 7% molybdenum by weight to about 15% molybdenum by weight, and most preferably 10% molybdenum by weight to 13% molybdenum by weight. This reaction is carried out at a temperature ranging from about 200 to 600° C., and preferably 300 to 500° C.; and, a pressure ranging from about 0.1 to 100 atmospheres, and preferably from about 0.5 to 5 atmospheres. The gas hourly space velocity for the reaction ranges from about 1,000 to 10,000,000 $hr^{-1}$, and preferably from about 20,000 to 1,000,000 $hr^{-1}$. This reaction allows for the production of nitrous oxide at a lower cost than current commercial methods. The present invention is also technically feasible using other methods of nitrous oxide production.

Table 1 shows data obtained using a catalyst containing molybdenum oxide supported on zirconia (11% Mo by weight). The data illustrate that selectivities to nitrous oxide of more than 70% can be achieved.

TABLE 1

| T (° C.) | Inlet Concentrations (ppm) | | | Outlet Concentrations (ppm) | | | | Selectivity to $N_2O$ |
|---|---|---|---|---|---|---|---|---|
| | $O_2$ | $NH_3$ | NO | $NH_3$ | NO | $N_2$ | $N_2O$ | |
| 300 | 10,000 | 500 | 500 | 385 | 385 | 91 | 15 | 14.5% |
| 350 | 10,000 | 500 | 500 | 322 | 321 | 121 | 50 | 29.0% |
| 400 | 10,000 | 500 | 500 | 252 | 269 | 109 | 125 | 53.5% |
| 450 | 10,000 | 500 | 500 | 167 | 228 | 95 | 205 | 68.4% |
| 500 | 10,000 | 500 | 500 | 92 | 211 | 99 | 250 | 71.7% |
| 500 | 10,000 | 200 | 200 | 84 | 132 | 25 | 68 | 71.4% |
| 500 | 10,000 | 907 | 907 | 481 | 560 | 115 | 277 | 71.6% |

The final step of the present invention is the coupling of methane in the presence of nitrous oxide to give ethylene or other higher hydrocarbons (Step 4). (Asami, K., Omata, K., Fujimoto, K., and Tominaga, H., *Energy and Fuels*, 2, 574 (1988); Mackie, J. C., and Hart, M. G.., *Energy and Fuels*, 4, 285 (1990); Voskresenkaya, E. N., Kurteeva, L. I., Pervyshina, G. G., and Anshits, A. G., *Catal. Today*, 24, 277 (1995); Otsuka and Wang, *Catal. Lett.*, 24, 85 (1994); Yamamoto, H., Chu, H. Y., Xu, M., Shi, C., and Lunsford, J. H., *J. Catal.*, 142, 325 (1993); Shepelev, S. S., and Lone, K. G., *J. Catal.*, 117, 362 (1989); Roguleva, V. G., Nikiphorova, M. A.., Maksimov, N. G., and Anshits, A. G., *Catal. Today*, 13,219 (1992); Pajonk and Manzalji, *Appl. Catal.* A, 108, 41 (1994).) The use of nitrous oxide allows for methane to be converted into higher order hydrocarbons with high selectivity and a minimal formation of carbon oxides. The source of nitrous oxide, provided from Step 3, allows for the production of higher order hydrocarbons at a lower cost than currently available methods.

The present invention also provides a method of balancing reaction heat requirements in a process for converting methane to higher order hydrocarbons. (See Table 2.) Energy consumption is a significant cost in the process of upgrading methane where nitrous oxide is used as an oxidizing agent. Energy is needed for the production of ammonia (equations (1a) and (1b)), a precursor reaction to the production of nitrous oxide. This cost is decreased in the present invention since heat is transferred from the remaining steps of the process which are extremely exothermic. The heat of reaction resulting from the conversion of ammonia to nitrous oxide is −527.8 kcal/mol (Steps 2 and 3). The heat of reaction resulting from the coupling of methane in the presence of nitrous oxide, to provide higher hydrocarbons, is −212.8 (Step 4). Therefore, the sum of the heat of these reactions is transferred to the endothermic synthesis reaction of ammonia from natural gas and nitrogen. This novel combination of reactions provide the production of higher order hydrocarbons from methane at a lower cost than presently available commercial methods.

TABLE 2

| Reaction | Heat of Reaction (kcal/mol) at 298 k |
|---|---|
| (1a) | 118.3 |
| (1b) | −87.7 |
| (2) | −216.6 |
| (3) | −311.2 |
| (4) | −212.8 |

We claim:

1. A method for converting methane to higher order hydrocarbons, which comprises the following steps:

(a) synthesizing ammonia from natural gas and nitrogen in the presence of a source of hydrogen;

(b) contacting ammonia with a catalyst which comprises platinum, in the presence of a source of oxygen, in order to convert it to nitric oxide and water;

(c) reacting ammonia and nitric acid in the presence of oxygen to produce nitrous oxide, whereby the reactants are contacted with a catalyst comprising molybdenum; and (d) coupling methane in the presence of nitrous oxide in order to produce higher order hydrocarbons.

2. The method of claim 1 wherein said source of hydrogen is steam reformed methane.

3. The method of claim 1, wherein the catalyst of step (c) further comprises zirconia, upon which the molybdenum is supported.

4. The method of claim 3, whereby nitrous oxide selectivity is greater than 70%.

5. The method of claim 1, wherein the catalyst of step (c) comprises from about 3 wt. % of molybdenum to about 20 wt. % of molybdenum.

6. The method of claim 1, wherein the catalyst of step (c) comprises from about 10 wt. % of molybdenum to about 13 wt. % of molybdenum.

7. The method of claim 1, wherein heat of reaction resulting from the conversion of ammonia to nitrous oxide and the coupling of methane is transferred to the synthesis of ammonia.

* * * * *